US012636441B2

(12) United States Patent
Jewell et al.

(10) Patent No.: US 12,636,441 B2
(45) Date of Patent: May 26, 2026

(54) TELESCOPING NEEDLE SHIELD WITH BLOOD EXPOSURE PREVENTION

(71) Applicant: Becton, Dickinson and Company, Franklin Lakes, NJ (US)

(72) Inventors: Derek Alan Jewell, Cottonwood Heights, UT (US); Yiping Ma, Layton, UT (US); John Stokes, Pleasant View, UT (US); Chad Alan Tagge, Sandy, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 794 days.

(21) Appl. No.: 16/735,139

(22) Filed: Jan. 6, 2020

(65) Prior Publication Data

US 2020/0215271 A1      Jul. 9, 2020

Related U.S. Application Data

(60) Provisional application No. 62/789,278, filed on Jan. 7, 2019.

(51) Int. Cl.
*A61M 5/32* (2006.01)
*A61M 5/31* (2006.01)
*A61M 25/06* (2006.01)

(52) U.S. Cl.
CPC ...... *A61M 5/3245* (2013.01); *A61M 25/0606* (2013.01); *A61M 25/0631* (2013.01); *A61M 25/0693* (2013.01); *A61M 2005/3109* (2013.01)

(58) Field of Classification Search
CPC .......... A61M 25/0606; A61M 25/0631; A61M 25/0612; A61M 25/0618; A61M 25/0625;
(Continued)

(56) References Cited

U.S. PATENT DOCUMENTS 4,850,961 A * 7/1989 Wanderer .......... A61M 25/0631
                                                    604/110
5,383,863 A * 1/1995 Mardones ........... A61M 5/3271
                                                    604/263

(Continued)

FOREIGN PATENT DOCUMENTS

EP          0599564          6/1994
KR      20150132423 A      11/2015
(Continued)

*Primary Examiner* — Chelsea E Stinson
*Assistant Examiner* — Leah J Swanson
(74) *Attorney, Agent, or Firm* — Kirton McConkie; Whitney Blair; Kevin Stinger

(57) ABSTRACT

A needle shield device may include a needle housing and a needle assembly slideably coupled to the needle housing. The needle housing may include a nose portion configured to be inserted into a catheter adapter and an elongated body having a distal end, a proximal end, and a slot disposed between the distal end and the proximal end of the elongated body. A distal portion of the slot may be sealed to prevent blood from leaking out of the needle housing. The needle assembly may include a needle grip, an introducer needle having a sharp distal tip and a proximal end, and a needle hub having a protuberance coupled to the needle grip and slideably fit within the slot. In response to movement of the needle assembly to a proximal position with respect to the needle housing, the sharp distal tip may be disposed within the needle housing.

20 Claims, 14 Drawing Sheets

(58) Field of Classification Search
CPC ........ A61M 2025/0175; A61M 5/3271; A61M
5/3245; A61M 2005/3109; A61M
25/0693; A61M 2025/0062; A61M 25/06;
A61M 5/321; A61M 5/3213; A61M
5/3243; A61M 5/3272
See application file for complete search history.

(56)                    References Cited

U.S. PATENT DOCUMENTS

| | | | | |
|---|---|---|---|---|
| 5,865,806 | A * | 2/1999 | Howell | A61M 25/0693 |
| | | | | 604/164.12 |
| 6,790,199 | B1 * | 9/2004 | Gianakos | A61M 25/0637 |
| | | | | 604/162 |
| 6,972,002 | B2 * | 12/2005 | Thorne | A61M 25/0631 |
| | | | | 604/164.08 |
| 7,530,965 | B2 * | 5/2009 | Villa | A61M 5/3273 |
| | | | | 604/110 |
| 8,617,112 | B2 * | 12/2013 | Tanabe | A61B 17/3403 |
| | | | | 604/164.08 |
| 2004/0116855 | A1 * | 6/2004 | Popov | A61M 25/0631 |
| | | | | 604/110 |
| 2004/0122373 | A1 * | 6/2004 | Botich | A61M 25/0631 |
| | | | | 604/164.12 |
| 2004/0138619 | A1 | 7/2004 | Kiehne | |
| 2004/0225260 | A1 | 11/2004 | Villa et al. | |
| 2016/0193453 | A1 | 7/2016 | Isaacson et al. | |
| 2016/0220791 | A1 * | 8/2016 | Akcay | A61B 5/150732 |

FOREIGN PATENT DOCUMENTS

| | | | | |
|---|---|---|---|---|
| WO | 00/02614 | | 1/2000 | |
| WO | WO-0002614 | A1 * | 1/2000 | A61M 25/0631 |

\* cited by examiner

TELESCOPING NEEDLE SHIELD WITH BLOOD EXPOSURE PREVENTION

RELATED APPLICATIONS

This application claims the benefit of U.S. Provisional Patent Application No. 62/789,278, filed on Jan. 7, 2019, and entitled TELESCOPING NEEDLE SHIELD WITH BLOOD EXPOSURE PREVENTION, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous catheter ("PIVC"). As its name implies, the over-the-needle PIVC may be mounted over an introducer needle having a sharp distal tip. The PIVC and the introducer needle may be assembled so that the distal tip of the introducer needle extends beyond the distal tip of the PIVC with the bevel of the needle facing away from skin of the patient. The PIVC and the introducer needle are generally inserted at a shallow angle through the skin into vasculature of the patient.

In order to verify proper placement of the introducer needle and/or the PIVC in the blood vessel, a clinician generally confirms that there is "flashback" of blood in a flashback chamber of a PIVC assembly. Once placement of the needle has been confirmed, the clinician may temporarily occlude flow in the vasculature and remove the introducer needle, leaving the PIVC in place for future blood withdrawal and/or fluid infusion.

There is a risk of accidental needle stick if the sharp distal tip of the introducer needle is not secured properly in a needle cover or shield. Thus, the PIVC assembly may be coupled to a needle shield. When the introducer needle is disposed within the needle shield, blood from the distal tip of the introducer needle may accumulate within the needle shield and may leak out of the needle shield, particularly when the needle shield includes a slot for telescoping between elements of the needle shield. Blood leaking out of the needle shield poses a risk of blood exposure to the clinician and others. The present disclosure presents devices, systems, and methods to prevent blood exposure resulting from blood leakage from a needle shield.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to needle shield devices and related systems and methods. In some embodiments, a needle shield device may include a needle housing. In some embodiments, the needle housing may include an elongated body, which may include a distal end, a proximal end, and a slot disposed between the distal end and the proximal end. In some embodiments, a distal portion of the proximal slot may be sealed or blocked, which may prevent blood from leaking out of the needle housing. In some embodiments, the needle housing may include a nose portion, which may be coupled to the distal end of the elongated body. In some embodiments, the nose portion may be configured to be inserted into a catheter adapter.

In some embodiments, the needle shield device may include a needle assembly, which may be slideably coupled to the needle housing. In some embodiments, the needle assembly may include an introducer needle, which may include sharp distal tip and a proximal end. In some embodiments, the needle assembly may include a needle grip and a needle hub. In some embodiments, the proximal end of the introducer needle may be secured within the needle hub.

In some embodiments, a protuberance of the needle hub may be coupled to the needle grip. In some embodiments, the protuberance may slideably fit within the slot. In some embodiments, the needle assembly may be moveable between a distal position and a proximal position with respect to the needle housing. In some embodiments, in response to movement of the needle assembly to the proximal position, the sharp distal tip may be disposed within the needle housing.

In some embodiments, the nose portion may include an elongated extension, which may seal the distal portion of the slot. In some embodiments, the elongated extension may be disposed on an outside of the elongated body. In some embodiments, the elongated extension may be disposed inside the elongated body. In some embodiments, the needle shield device may include adhesive tape adhered to the elongated body. In some embodiments, the adhesive tape may seal the distal portion of the slot.

In some embodiments, the needle shield device may include an insert, which may be inserted or disposed within the elongated body. In some embodiments, the insert may include a tubular sleeve. In some embodiments, the insert may include a reservoir. In some embodiments, the insert may seal the distal portion of the slot. In some embodiments, the insert and the nose portion may be monolithically formed as a single unit.

In some embodiments, the needle hub may include a flashback chamber. In some embodiments, the flashback chamber may extend adjacent or beyond the proximal end of the needle grip. In some embodiments, the nose portion may include one or more channels configured to direct blood away from the slot.

In some embodiments, a catheter system may include the needle shield device and a catheter assembly. In some embodiments, the catheter assembly may include a catheter adapter, which may include a distal end, a proximal end, and a lumen extending between the distal end and the proximal end. In some embodiments, the catheter assembly may include a catheter, which may include a distal end and a proximal end. In some embodiments, the catheter may include a PIVC. In some embodiments, the proximal end of the catheter may be secured within the catheter adapter. In some embodiments, the introducer needle may include a notch, which may be proximate the distal end of the catheter.

In some embodiments, the needle housing may include a septum disposed within the elongated body and/or the nose portion. Additionally or alternatively, in some embodiments, the needle housing may include a lube disposed within the nose portion. In some embodiments, the septum and/or the lube may prevent blood from the introducer needle from leaking out of the needle shield device.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1A:
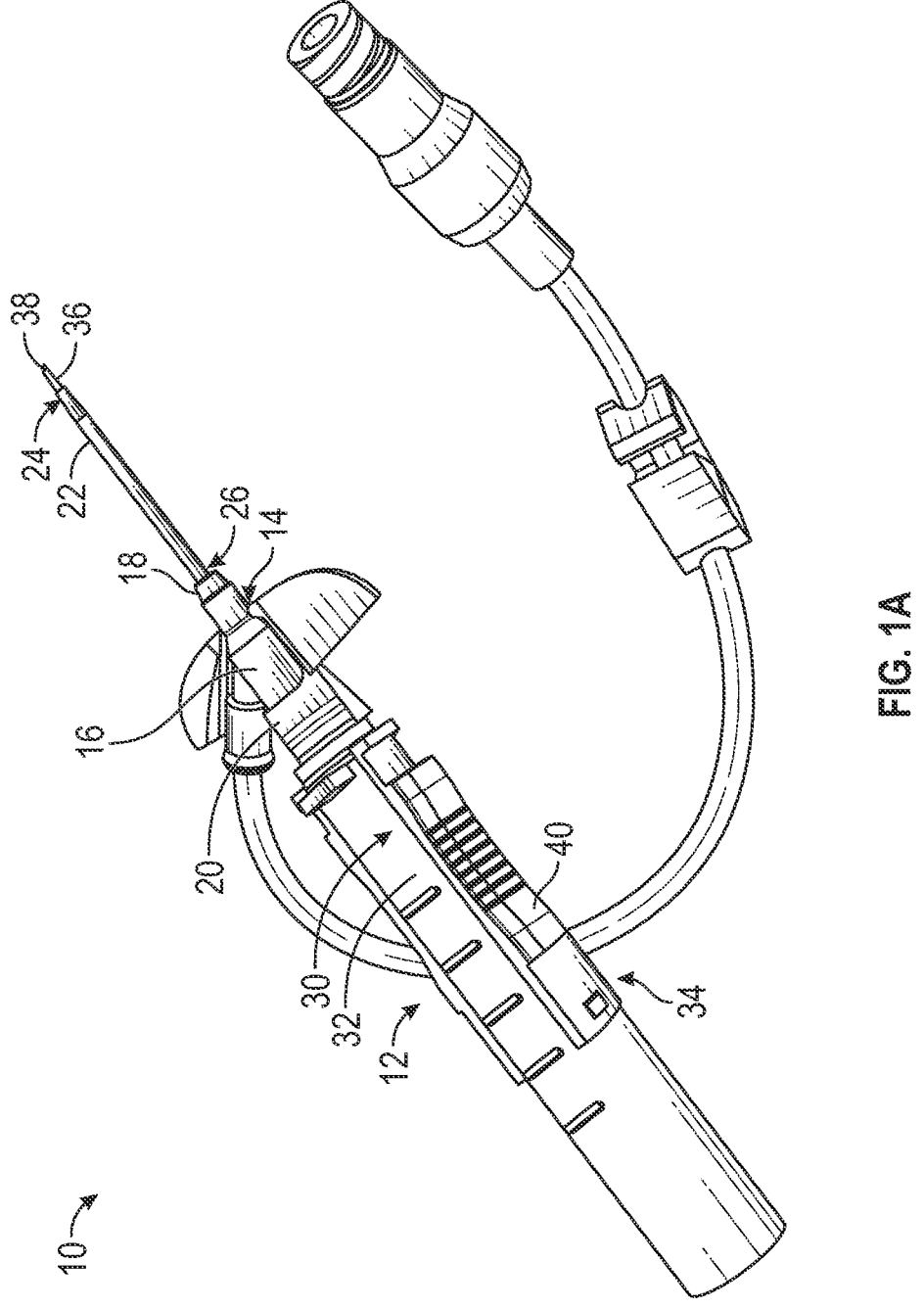
FIG. 1A is an upper perspective view of an example catheter system having an example needle shield device, according to some embodiments.

Referring to FIG. 1A, in some embodiments, a catheter system 10 may include a needle shield device 12 and a catheter assembly 14. In some embodiments, the catheter assembly 14 may include a catheter adapter 16, which may include a distal end 18, a proximal end 20, and a lumen extending between the distal end 18 and the proximal end 20. In some embodiments, the catheter assembly 14 may include a catheter 22, which may include a distal end 24 and a proximal end 26. In some embodiments, the catheter 22 may include a peripheral intravenous catheter ("PIVC"). In some embodiments, the proximal end 26 of the catheter 22 may be secured within the catheter adapter 16.

In some embodiments, the catheter system 10 may be integrated, having an integrated extension tube, such as, for example, the BD NEXIVA™ Closed IV Catheter System, the BD NEXIVA™ DIFFUSICS™ Closed IV Catheter System, the BD PEGASUS™ Safety Closed IV Catheter System, or other integrated catheter systems. An example of an integrated catheter system 10 is illustrated in FIG. 1A. In some embodiments, the catheter system 10 may be non-integrated. The catheter system 10 may include one or more features of the safety catheter assembly described in U.S. patent application Ser. No. 15/012,013, filed Feb. 1, 2016, entitled "RELEASABLE CATHETER HUB RETAINER," which is hereby incorporated by reference in its entirety.

In some embodiments, the needle shield device 12 may include a needle housing 30, which may be removably coupled to the catheter adapter 16. In some embodiments, the needle housing 30 may include an elongated body 32. In some embodiments, the needle shield device 12 may include a needle assembly 34, which may be slideably coupled to the needle housing 30.

In some embodiments, the needle assembly 34 may include an introducer needle 36, which may include sharp distal tip 38. In some embodiments, the introducer needle 36 may extend through the catheter 22 when the catheter system 10 is in an insertion position ready for insertion into vasculature of a patient, as illustrated, for example, in FIG. 1A. In some embodiments, the needle assembly 34 may include a needle grip 40, which the clinician may grip and move proximally to withdraw the introducer needle 36 from the vasculature once placement of the catheter 22 within the vasculature is confirmed.

In some embodiments, placement of the catheter 22 within the vasculature may be confirmed via blood flashback. In some embodiments, in response to the introducer needle 36 being inserted into the vasculature of the patient, blood flashback may flow through the sharp distal tip 38 of the introducer needle 36 and out of a distal notch of the introducer needle 36 into a portion of the catheter system 10. For example, the blood flashback may flow through the sharp distal tip 38 and out of the distal notch into a space between an exterior surface of the introducer needle 36 and an interior surface of the catheter 22.

Figure 1B:
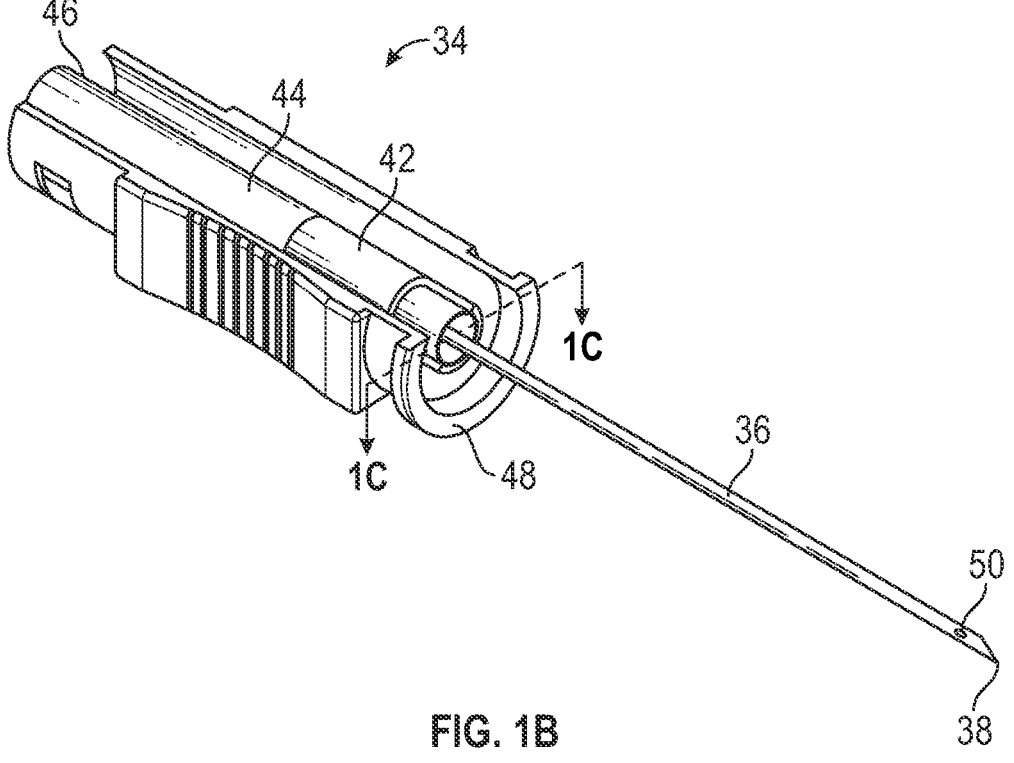
FIG. 1B is an upper perspective view of an example needle assembly of the needle shield device, according to some embodiments.

Referring now to FIG. 1B, the needle assembly 34 is illustrated, according to some embodiments. In some embodiments, the needle assembly 34 may include a needle hub 42. In some embodiments, a proximal end of the introducer needle 36 may be secured within the needle hub 42. In some embodiments, the needle hub 42 may include a flashback chamber 44. In some embodiments, in response to the introducer needle 36 being inserted into the vasculature of the patient, blood flashback may flow through the sharp distal tip 38 of the introducer needle 36 and into the flashback chamber 44. In some embodiments, at least a portion of the flashback chamber 44 and/or at least a portion of the needle housing 30 may be transparent such that the clinician may visualize the blood within the flashback chamber 44. In some embodiments, the flashback chamber 44 may include a material that enables air to vent from the flashback chamber 44 as blood fills the flashback chamber 44 but inhibits the blood from passing from the flashback chamber 44.

In some embodiments, the needle grip 40 may include a C-shaped cross-section configured to fit around an outer surface of the needle housing 30 in a manner that inhibits the needle hub 42 from readily separating from the needle housing 30, yet enables the needle hub 42 and needle housing 30 to slide relative to one another with minimal resistance as the needle assembly 34 moves from a distal position to a proximal position.

In some embodiments, the needle grip 40 may include one or more ridges or protrusions, which may aid in gripping of the needle grip 40 by the clinician. In some embodiments, the needle grip 40 may include a proximal end 46 and a distal end 48. In some embodiments, the introducer needle 36 may include the distal notch 50. In some embodiments, the flashback chamber 44 may extend adjacent the proximal end 46 of the needle grip 40, which may increase a volume of the flashback chamber 44 and reduce pressure at the distal notch 50.

In some embodiments, the distal notch 50 may be near or proximate the distal end of the catheter 22, which may decrease a length of time the distal notch 50 is disposed proximal to a septum 68 of the catheter adapter 16 (illustrated, for example in FIGS. 2A and 3A) and decrease a likelihood of blood leakage from the catheter system 10. In some embodiments, the distal notch 50 may be disposed a short distance from the distalmost point of the sharp distal tip 38. In some embodiments, the distal notch 50 may be disposed distal to the septum 68 of the catheter adapter 16 when the needle assembly 34 is moved up to ½ way between the distal position and the proximal position.

Figure 1C:
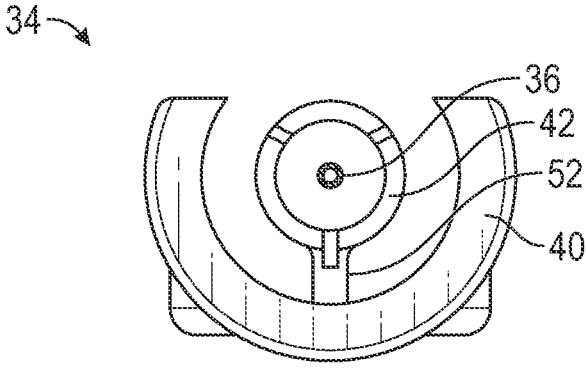
FIG. 1C is a cross-sectional view of the needle assembly along the line 1C-1C of FIG. 1B, according to some embodiments.
Figure 1D:
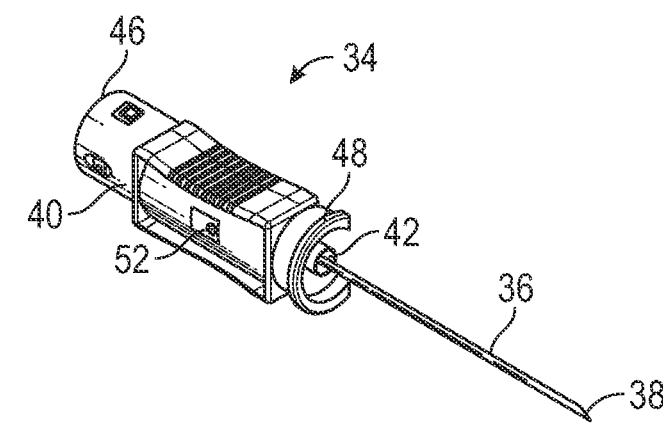
FIG. 1D is a bottom perspective view of the needle assembly, according to some embodiments.

Referring now to FIGS. 1C-1D, in some embodiments, the needle hub 42 may include a guide pin or protuberance 52 that may be coupled to the needle grip 40. In some embodiments, the protuberance 52 may prevent the needle hub 42 from rotating about a longitudinal axis of the needle housing 30. In some embodiments, the needle hub 42, the protuberance 52, and the needle grip 40 may be monolithically formed as a single unit.

Figure 1E:
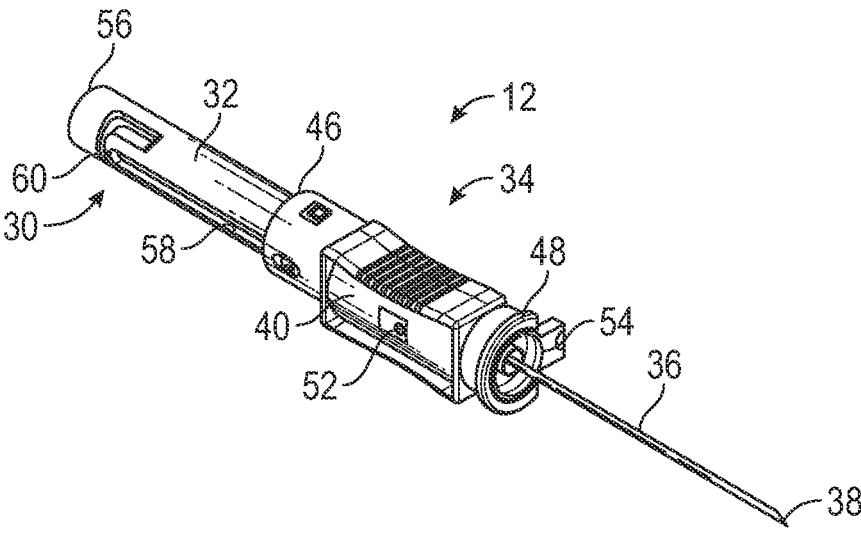
FIG. 1E is a bottom perspective view of the needle shield device in which the needle assembly is coupled to an example needle housing, illustrating the a nose portion removed and the needle assembly in a distal position with respect to the housing shield, according to some embodiments.
Figure 1F:
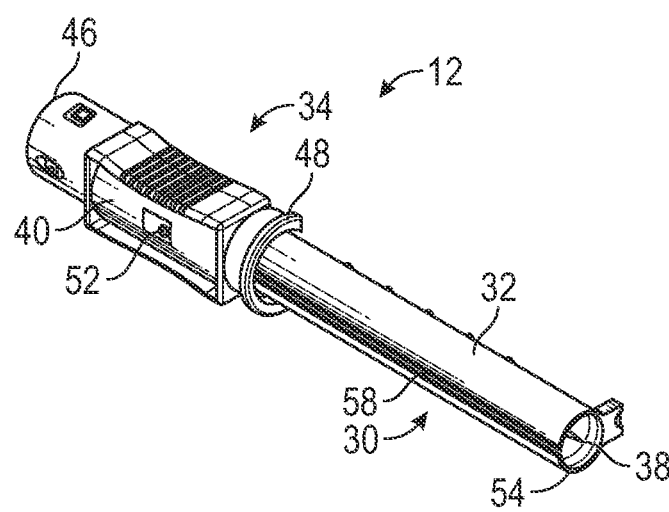
FIG. 1F is a bottom perspective view of the needle shield device, illustrating the nose portion removed and the needle assembly in a proximal position with respect to the needle housing, according to some embodiments.

Referring now to FIGS. 1E-1F, the elongated body 32 may include a distal end 54, a proximal end 56, and a slot 58 disposed between the distal end 54 and the proximal end 56. In some embodiments, the protuberance 52 may slidably fit within the slot 58. In some embodiments, the needle assembly 34 may be moveable with respect to the needle housing 30 between the distal position, illustrated, for example in FIG. 1E, and the proximal position, illustrated, for example in FIG. 1F. In some embodiments, in response to movement of the needle assembly 34 to the proximal position, the sharp distal tip 38 may be disposed within the needle housing 30, as illustrated, for example, in FIG. 1F.

In some embodiments, after positioning in the proximal or safe position, return movement of the needle assembly 34 back toward the distal or ready for use position may be inhibited by a needle lock 60. In some embodiments, the needle lock 60 may thus be configured to interlock the needle hub 42 to the needle housing 30 in the proximal position. In some embodiments, the needle lock 60 may be positioned on a proximal portion of the needle housing 30 at a proximal end of the slot 58 to engage the protuberance 52.

In some embodiments, several different types of locking mechanisms can be used for this purpose. For example, the slot 58 may include a bottleneck that may have a narrower width than a portion of the slot 58 adjacent the bottleneck. In some embodiments, the protuberance 52 of the needle hub 42 may be triangular or wedge-like in shape where an apex of the wedge faces the bottleneck when in distal position. In some embodiments, when an external force is applied to the needle hub 42 in an effort to slide it into the proximal position, the apex of the wedge of the protuberance 52 may come into contact with the bottleneck. In some embodiments, the bottleneck may include a width narrower than that of the protuberance 52 and may initially resist movement of the protuberance 52 through the bottleneck. In some embodiments, with sufficient force the wedge-shape protuberance 52 may cause the bottleneck to temporarily deform, thereby enabling the protuberance 52 to pass through the bottleneck to lock in the proximal position relative to the needle housing 30.

In some embodiments, the slot 58 may be disposed on a bottom of the elongated body 32, as illustrated, for example, in FIGS. 1E-1F. In some embodiments, the bottom of the elongated body 32 may face the skin of the patient when the catheter system 10 is inserted within the vasculature of the patient. In some embodiments, the slot 58 may be disposed at another location of the elongated body 32.

Figure 1G:
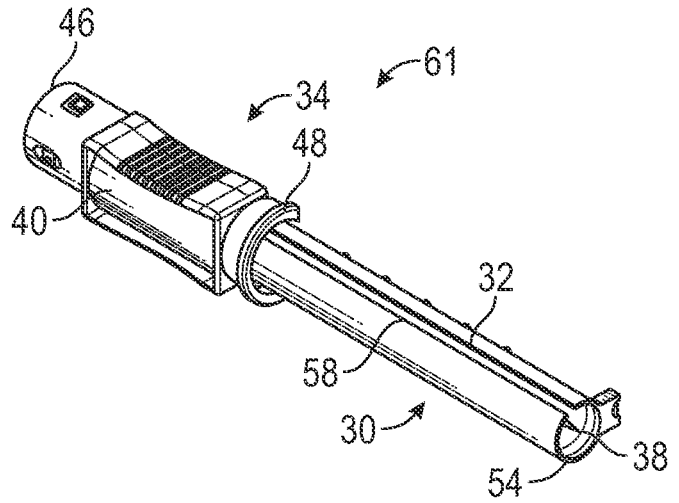
FIG. 1G is a bottom perspective view of another needle shield device, illustrating the nose portion removed and the needle assembly in a proximal position with respect to the needle housing, according to some embodiments.
Figure 1H:
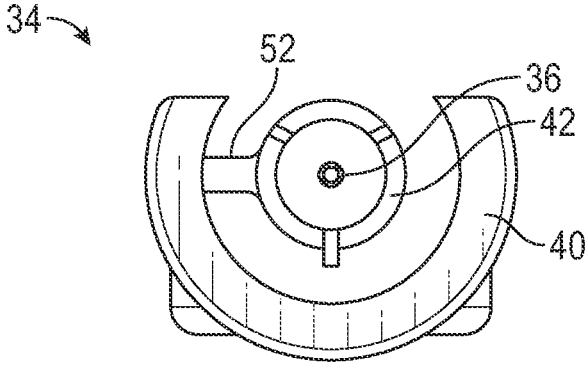
FIG. 1H is a cross-sectional view of an example needle assembly that includes the other needle shield device, according to some embodiments.

Referring now to FIGS. 1G-1H, in some embodiments, the slot 58 of a needle shield device 61 may be disposed on a top or a side of the elongated body 32, which may reduce blood leakage through the slot 58 due to gravity, compared to a particular slot 58 on the bottom of the elongated body 32. In some embodiments, the protuberance 52 connecting the needle hub 42 and the 40 needle grip may be disposed on the side or the top of the needle shield device 61. In some embodiments, the needle shield device 61 may be similar or identical to the needle shield device 12 in terms of one or more included features and/or operation. In some embodiments, a bevel of the sharp distal tip 38 may face towards the top of the elongated body 42 and the top of the needle shield device 61. In some embodiments, the bottom of the elongated body 42 and the bottom of the needle shield device 61 may be closest to skin of the patient when the needle shield device 61 is inserted into the patient.

Referring now to FIGS. 2A-3B, in some embodiments, the needle housing 30 may include a nose portion 62, which may be coupled to the distal end 54 of the elongated body 32. In some embodiments, the nose portion 62 may be configured to be inserted into the catheter adapter 16. In some embodiments, the needle housing 30 may be coupled to the catheter adapter 16 via a connector of the needle housing 30. In some embodiments, the connector may include a luer adapter, such as a slip or thread male or female luer adapter, or a non-luer adapter.

Figures 2A, 2B:
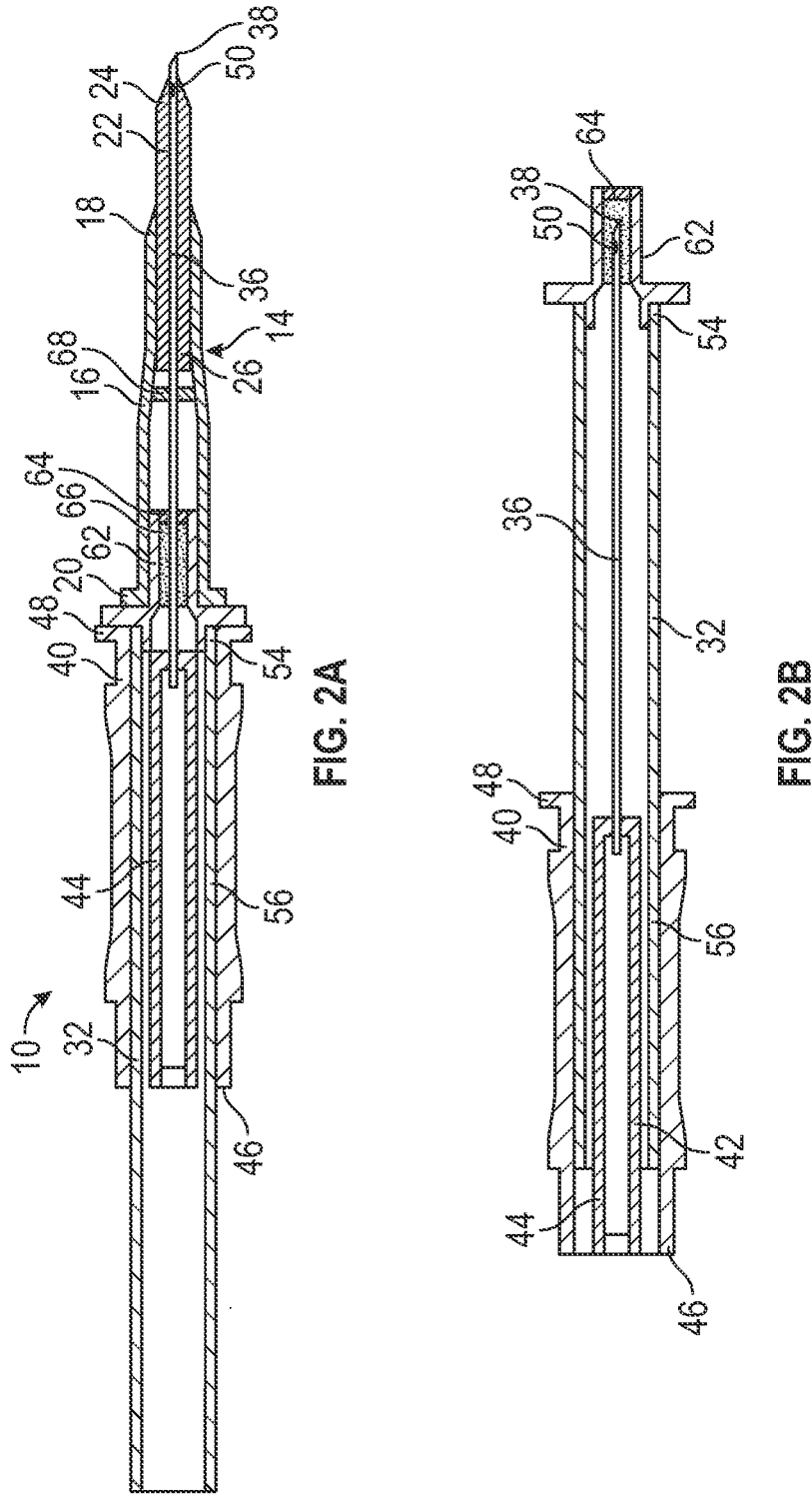
FIG. 2A is a cross-sectional view of the catheter system, illustrating an example septum disposed within the needle housing, an example nose portion, and the needle assembly in the distal position with respect to the needle housing, according to some embodiments.
FIG. 2B is a cross-sectional view of the needle shield device, illustrating the septum disposed within the needle housing, the nose portion, and the needle assembly in the distal position with respect to the needle housing, according to some embodiments.
Figures 3A, 3B:
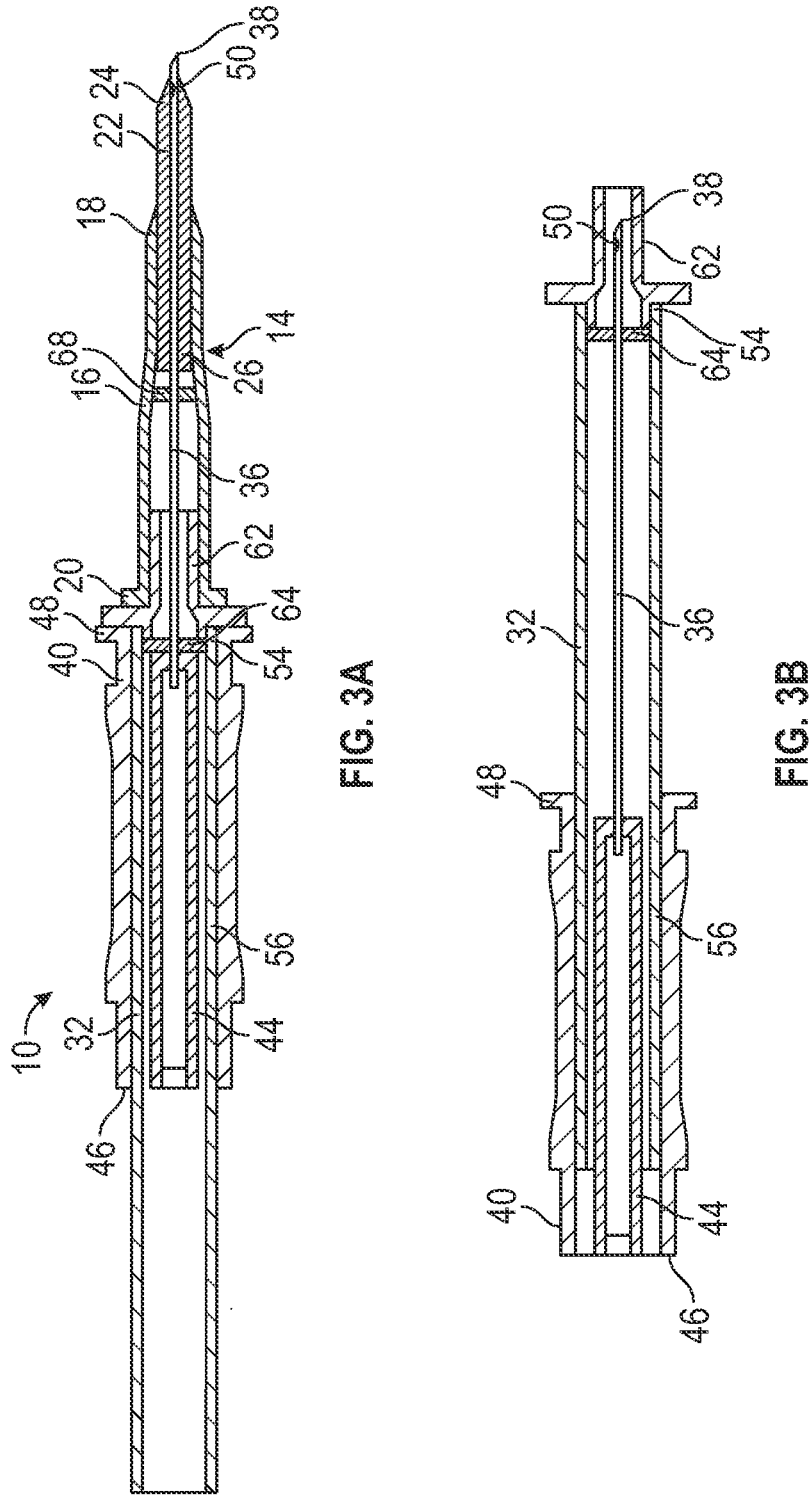
FIG. 3A is a cross-sectional view of the catheter assembly, illustrating another example septum disposed within the needle housing and illustrating the needle assembly in the distal position with respect to the needle housing, according to some embodiments.
FIG. 3B is a cross-sectional view of the needle shield device, illustrating the other example septum and illustrating the needle assembly in the proximal position with respect to the needle housing, according to some embodiments.

In some embodiments, the needle housing 30 may include a septum 64 disposed within the elongated body 32 and/or the nose portion 62. In some embodiments, the septum 64 may be replaced with a membrane. FIGS. 2A-2B illustrate the septum 64 disposed within the nose portion 62, according to some embodiments. FIGS. 3A-3B illustrate the septum 64 disposed within the elongated body 32, according to some embodiments. In these and other embodiments, the needle housing 30 may include a lube 66 disposed within the nose portion 62. In some embodiments, the septum 64 and/or the lube 66 may prevent blood from the introducer needle 36 from leaking out of the needle shield device 12. A septum 68 of the catheter adapter 14 is illustrated in FIGS. 2A and 3A, according to some embodiments.

Figure 4:
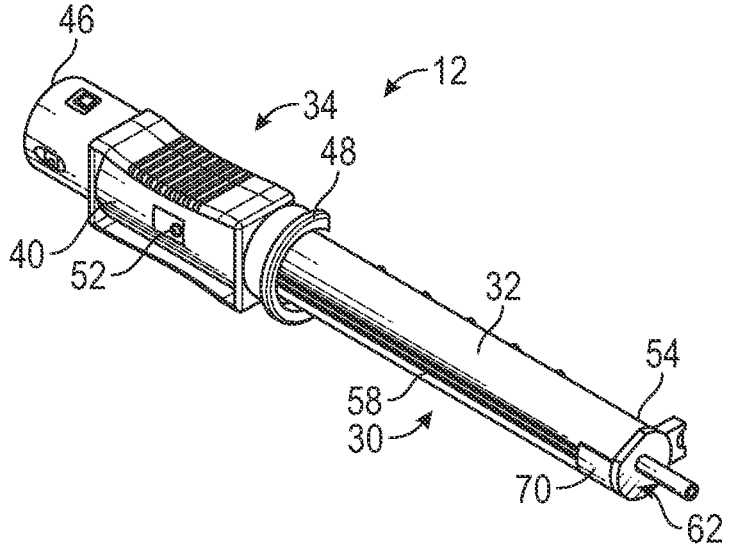
FIG. 4 is a bottom perspective view of the needle shield device, illustrating example adhesive tape, according to some embodiments.
Figure 5A:
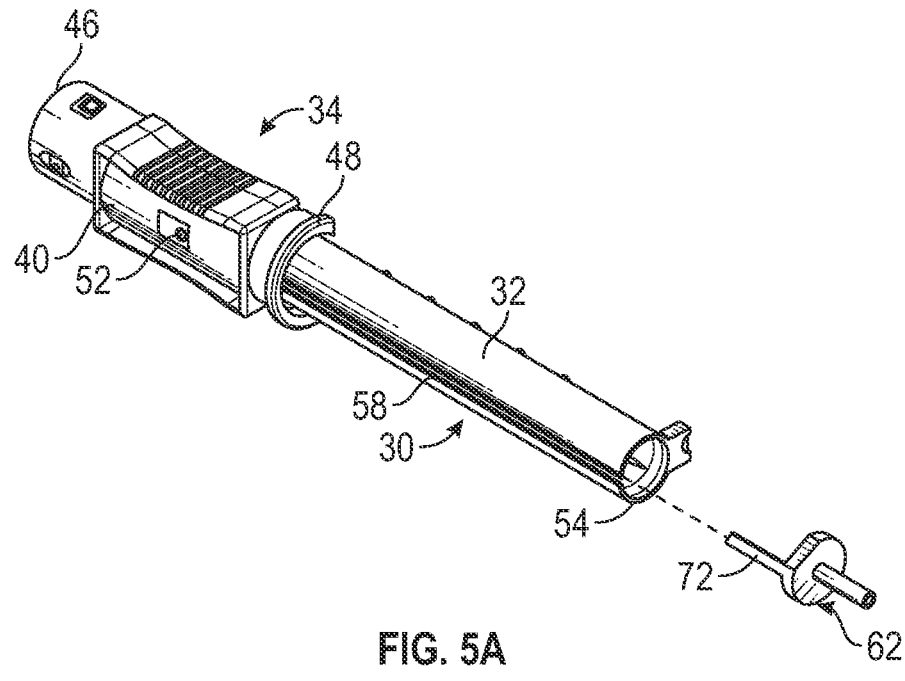
FIG. 5A is an exploded view of the needle shield device, illustrating another example nose, according to some embodiments.
Figure 5B:
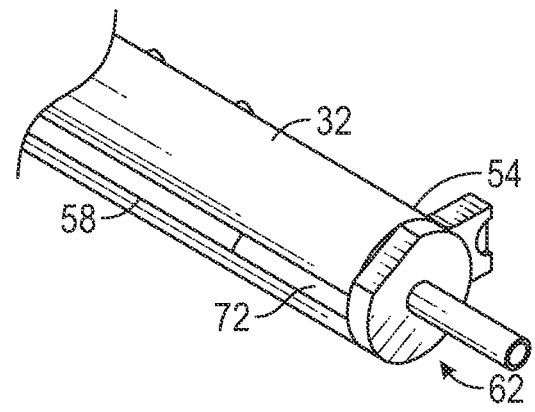
FIG. 5B is bottom perspective view of the needle shield device, illustrating the other nose of FIG. 5A coupled to the needle housing, according to some embodiments.
Figure 5C:
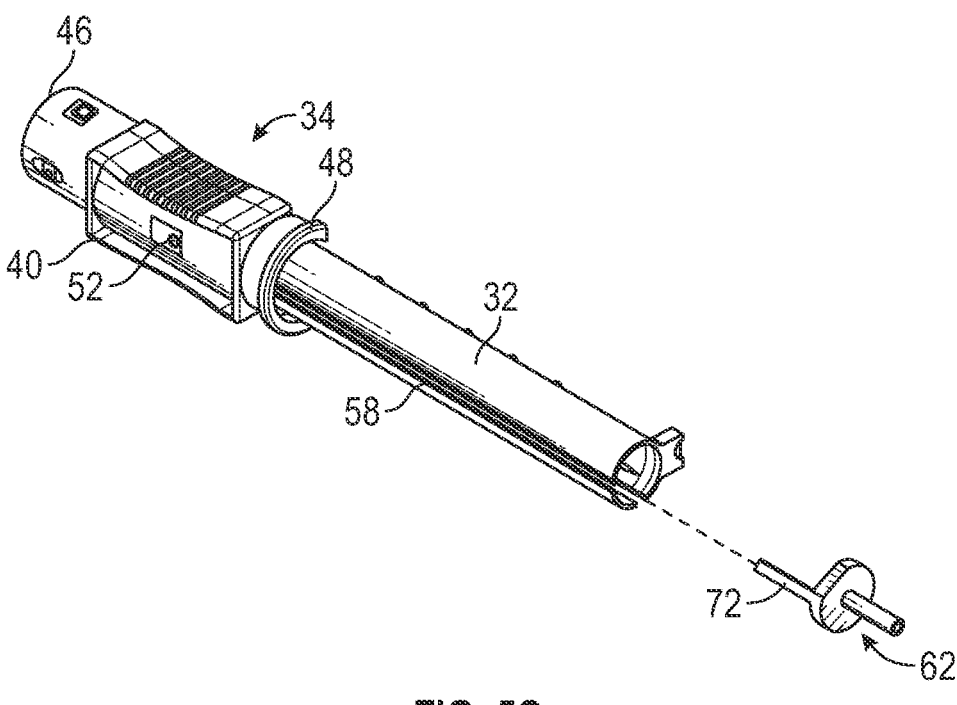
FIG. 5C is an exploded view of the needle shield device, illustrating another example nose, according to some embodiments.
Figure 5D:
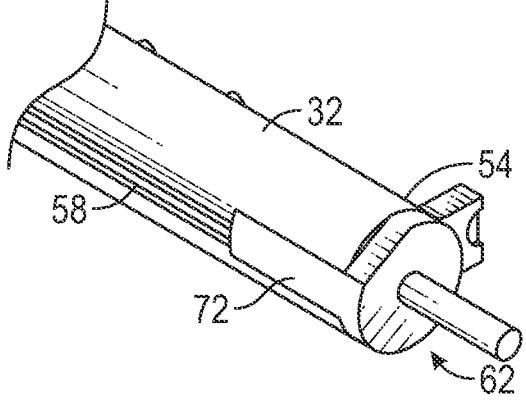
FIG. 5D is a bottom perspective view of the needle shield device, illustrating the other nose of FIG. 5C coupled to the needle housing, according to some embodiments.

Referring now to FIG. 4, in some embodiments, the needle shield device 12 may include adhesive tape 70 adhered to the elongated body 32. In some embodiments, the adhesive tape 70 may seal the distal portion of the slot 58. In some embodiments, the adhesive tape 70 may be proximate the nose portion 62. In some embodiments, an entirety of the slot 58 distal to a proximal end of the adhesive tape 70 may be sealed.

Referring now to FIGS. 5A-5D, in some embodiments, the nose portion 62 may include an elongated extension 72, which may seal the distal portion of the slot 58. In some embodiments, the elongated extension 72 may be disposed inside the elongated body 32, as illustrated, for example, in FIGS. 5A-5B. In some embodiments, the elongated extension 72 may be disposed on an outside of the elongated body 32, as illustrated, for example in FIGS. 5C-5D.

Referring now to FIGS. 6A-7B, in some embodiments, the needle shield device 12 may include an insert 74, which may be inserted or disposed within the elongated body 32.

In some embodiments, the insert 74 may seal the distal portion of the slot 58. In some embodiments, the proximal end 46 of the needle grip 40 may be open or may be closed, as illustrated, for example in FIGS. 6B-7B. In some embodiments, the flashback chamber 44 may extend adjacent or proximate the closed proximal end 46.

Figure 6A:
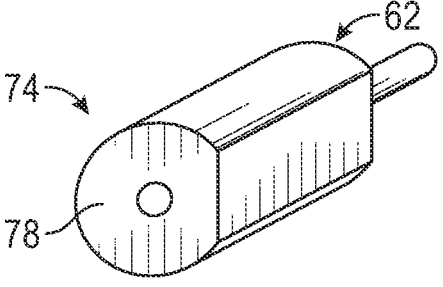
FIG. 6A is a bottom perspective of another example nose, according to some embodiments.
Figures 6B, 7A, 7B:
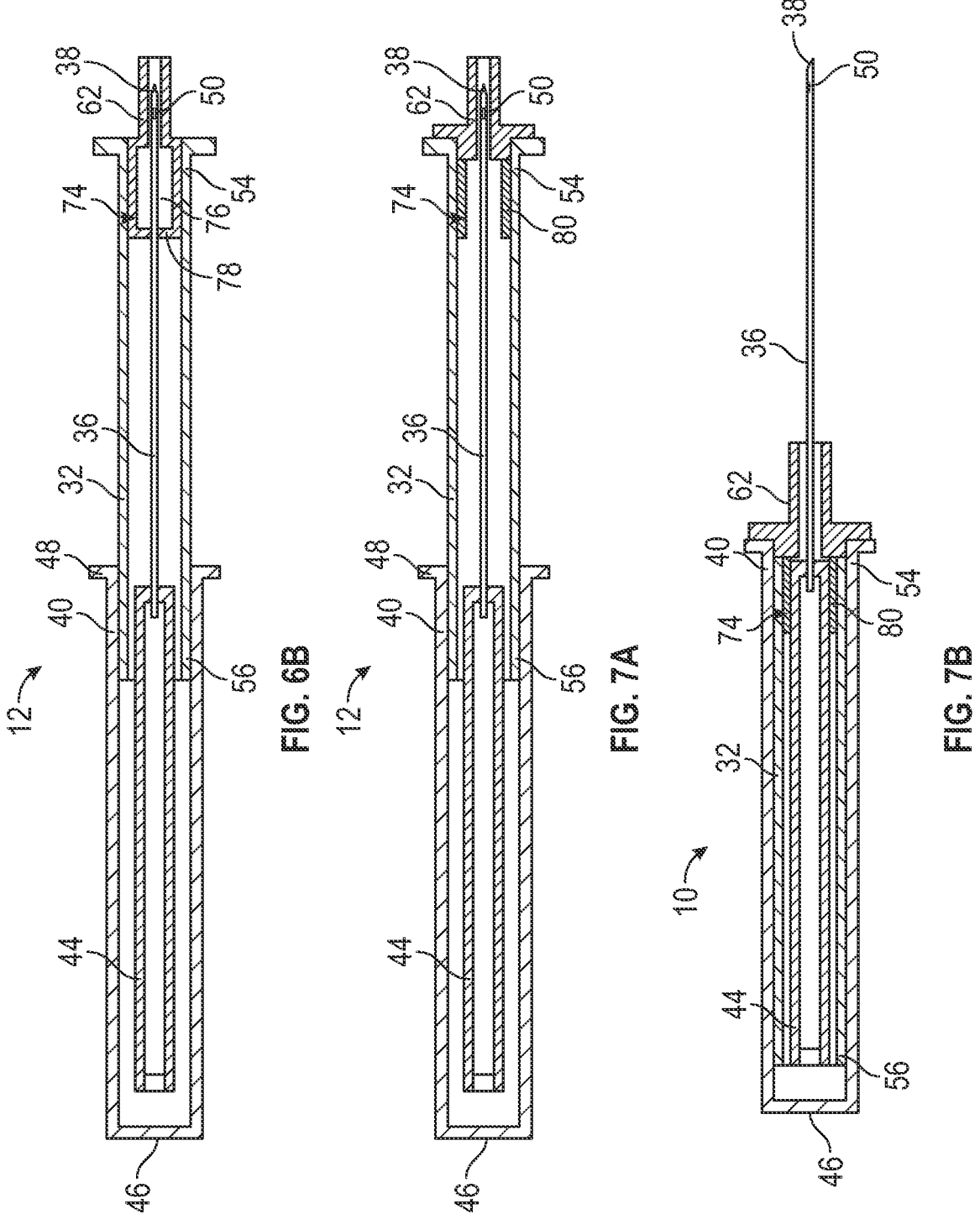
FIG. 6B is a cross-sectional view of the needle shield device illustrating the other nose of FIG. 6A and illustrating the needle assembly in the proximal position with respect to the needle housing, according to some embodiments.
FIG. 7A is a cross-sectional view of an example tubular sleeve disposed with the needle shield device and the needle assembly in the proximal position with respect to the needle housing, according to some embodiments.
FIG. 7B is a cross-sectional view of the tubular sleeve disposed with the needle shield device and the needle assembly in the distal position with respect to the needle housing, according to some embodiments.

Referring now to FIG. 6A-6B, in some embodiments, the insert 74 and the nose portion 62 may be monolithically formed as a single unit. In other embodiments, the insert 74 and the nose portion 62 may be separate pieces. In some embodiments, the insert 74 may include a reservoir 76. In some embodiments, the reservoir 76 may include an annular flange 78 to facilitate containment of blood within the reservoir 76. Referring now to FIG. 7A-7B, in some embodiments, the insert 74 may include a tubular sleeve 80, which may seal the distal portion of the slot 58.

Figure 8:
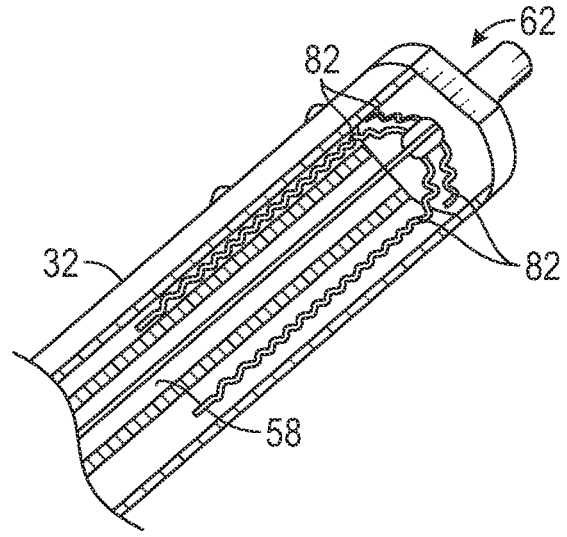
FIG. 8 is a partial cutaway view of the needle housing, illustrating example grooves, according to some embodiments.

Referring now to FIG. 8, in some embodiments, the nose portion 62 may include one or more grooves 82 configured to direct blood away from the slot 58. In some embodiments, the grooves 82 may extend along a proximal face of the nose portion 62 and/or the elongated body 32. In some embodiments, the grooves 82 may extend proximal to a distal end of the slot 58 and/or along a substantial portion of the slot 58. In some embodiments the grooves 82 may extend along all or a portion of a length of the nose portion 62.

Figure 9A:
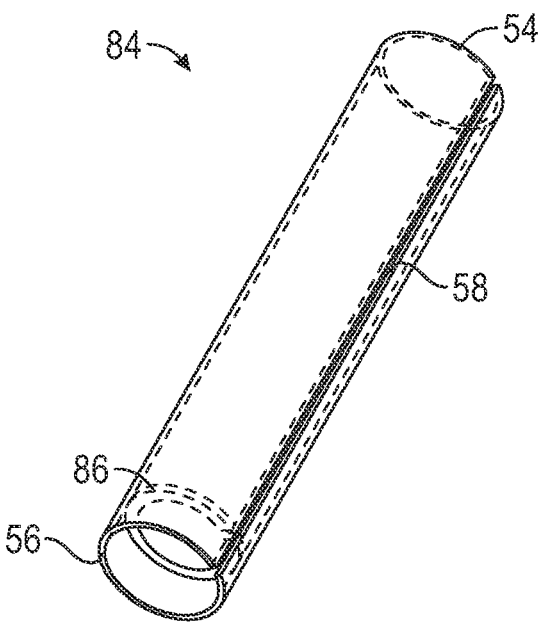
FIG. 9A is an upper perspective view of another example elongated body, according to some embodiments.

Referring now to FIG. 9A, in some embodiments, an elongated body 84 may include a slot 58 extending entirely or partially along a length of the elongated body 84. In some embodiments, the elongated body 84 may include or correspond to the elongated body 32 of one or more of the previous FIGS. 1-8. For example, the elongated body 84 may include the needle lock 60, illustrated, for example, in FIG. 1E, at a proximal end of the slot 58. As another example, in some embodiments, the nose portion 62, illustrated, for example, in FIG. 2B, may be coupled to the distal end 54 of the elongated body 84. In some embodiments, the elongated body 84 may include an internal ledge or step 86. In some embodiments, the step 86 may be fixed within the elongated body 84. In some embodiments, the step 86 may be integrally formed with the elongated body 84.

Figure 9B:
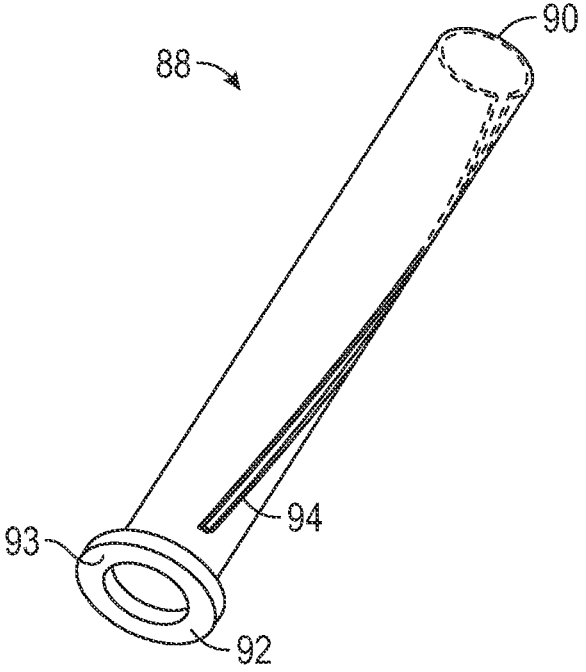
FIG. 9B is an upper perspective view of an example inner sleeve, according to some embodiments.

Referring now to FIG. 9B, an example inner sleeve 88 is illustrated, according to some embodiments. In some embodiments, the inner sleeve 88 may include a distal end 90, a proximal end 92, and a slot 94 disposed between the distal end 90 and the proximal end 92. In some embodiments, the slot 94 may extend through the distal end 90. In some embodiments, the slot 94 may be curved. In some embodiments, the inner sleeve 88 may include a flange 93, which may be configured to contact the internal step 86 of the elongated body 84 when the inner sleeve 88 is disposed within the elongated body 84. In some embodiments, the inner sleeve 88 may be secured within the elongated body 84 in any number of ways that facilitate the elongated body 84 and the inner sleeve 88 moving together in a proximal direction and distal direction while the inner sleeve 88 rotates with respect to the elongated body 84.

Figure 9C:
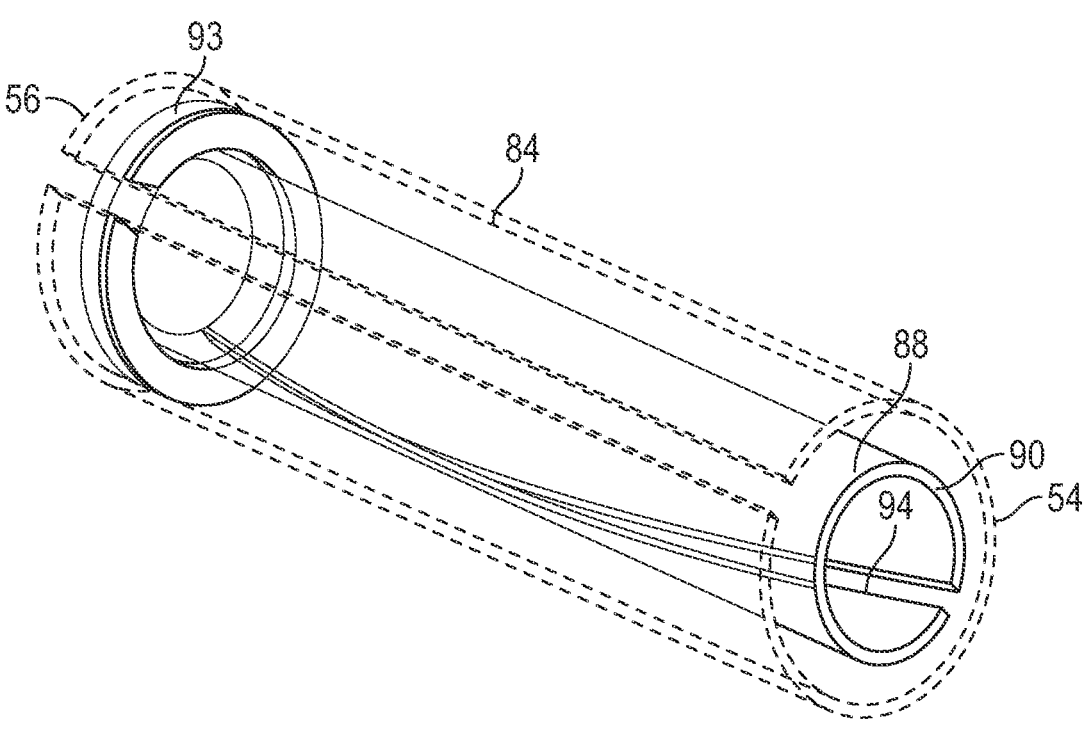
FIG. 9C is an upper perspective view of the inner sleeve of FIG. 9B disposed within the elongated body of FIG. 9A during assembly, according to some embodiments.
Figure 9D:
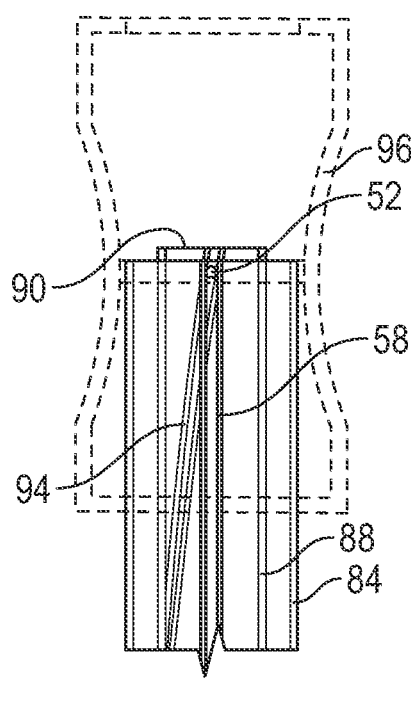
FIG. 9D is an upper perspective view the inner sleeve of FIG. 9B and the elongated body of FIG. 9A being placed within an example needle grip during assembly, according to some embodiments.

Referring now to FIG. 9C, the inner sleeve 88 is illustrated within the elongated body 84 prior to coupling to a needle assembly, according to some embodiments. Referring now to FIG. 9D, in some embodiments, the inner sleeve 88 and the elongated body 84 may be placed within a needle grip 96 during assembly. In some embodiments, the needle grip 96 may include or correspond to the needle grip 40 illustrated, for example, in one or more of FIGS. 1-8. In some embodiments, the needle grip 96 may be part of the needle assembly 34, although the needle assembly 34 is not fully illustrated in FIGS. 9D-9F for simplicity and illustration purposes. In some embodiments, the flashback chamber 44, illustrated, for example, in FIG. 1B, may be disposed within the inner sleeve 88.

Figures 9E, 9F:
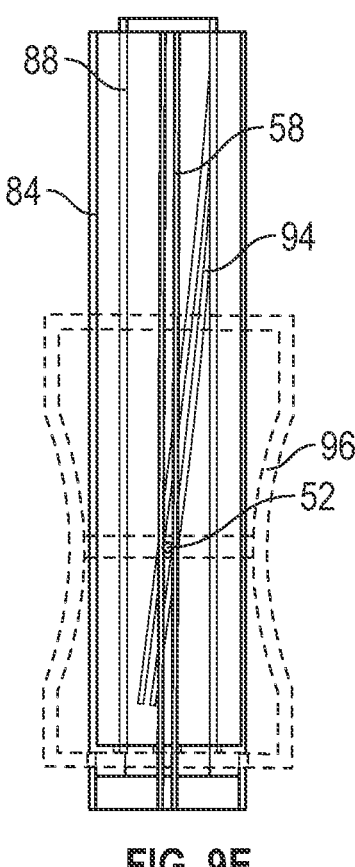
FIG. 9E is an upper perspective view of the needle grip of FIG. 9D disposed in the proximal position, according to some embodiments.
FIG. 9F is a cross-sectional view illustrating a portion of the inner sleeve of FIG. 9B disposed within a portion the elongated body of FIG. 9A, according to some embodiments.

Referring now to FIG. 9E, the needle grip 96 is illustrated in the proximal position, according to some embodiments. In some embodiments, the protuberance 52 may be slidably positioned through the slot 58 and the slot 94, as illustrated in FIGS. 9D-9E. In some embodiments, in response to movement of the needle grip 96 to the proximal position and/or the distal position, the inner sleeve 88 may rotate with respect to the elongated body 84, which may be held in a hand of the clinician and may not rotate. In some embodiments, in response to movement of the needle grip 96 to the proximal position, the inner sleeve 88 may rotate with respect to the elongated body 84 such that a distal portion of the slot 94 is not aligned with a distal portion of the slot 58 and the distal portion of the slot 58 is sealed by the elongated body 84. Thus, in some embodiments, the inner sleeve 88 may prevent blood leakage from at least a portion of the slot 58.

Referring now to FIG. 9F, the inner sleeve 88 is illustrated within the elongated body 84. In some embodiments, the internal step 86 may abut the flange 93 facilitating movement of the internal sleeve 88 in the proximal direction in response to movement of the elongated body 84 to the proximal position.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A needle shield device comprising:
a needle assembly that includes a needle hub, a needle grip disposed around the needle hub and an introducer needle extending distally from the needle hub; and
a needle housing to which the needle assembly is slidably coupled such that, when the needle assembly is slid from a distal position to a proximal position relative to the needle housing, a distal tip of the introducer needle is retracted into the needle housing;
wherein the needle housing comprises:
an elongated body having a straight slot that extends from a proximal end of the elongated body to a distal end of the elongated body; and
an inner sleeve that is positioned within the elongated body and configured to rotate within the elongated body, the inner sleeve including a curved slot that extends from a proximal end of the inner sleeve to a distal end of the inner sleeve;
wherein the needle grip includes a protuberance that extends inwardly through the straight slot of the elongated body and the curved slot of the inner sleeve such that, as the needle assembly is slid from the distal position to the proximal position, the protuberance slides within the straight slot and the curved slot to thereby cause the inner sleeve to rotate relative to the elongated body, the rotation of the inner sleeve relative to the elongated body causing the inner sleeve to cover the straight slot at a distal end of the elongated body.

2. The needle shield device of claim 1, wherein the elongated body includes an internal step towards the proximal end of the elongated body and the inner sleeve includes a flange at the distal end of the inner sleeve, and wherein the flange contacts the internal step when the inner sleeve is positioned within the elongated body.

3. The needle shield device of claim 1, wherein the protuberance is positioned at a distal end of the straight slot and a distal end of the curved slot when the needle housing is in the distal position.

4. The needle shield device of claim 1, wherein the needle housing includes a nose portion that is coupled to the distal end of the elongated body.

5. The needle shield device of claim 4, wherein the nose portion is configured to couple to a catheter adapter.

6. The needle shield device of claim 4, wherein the nose portion includes one or more grooves that are configured to direct blood away from the straight slot.

7. The needle shield device of claim 4, wherein the nose portion includes an elongated extension that seals a distal portion of the straight slot.

8. The needle shield device of claim 1, wherein the needle housing includes a septum disposed within the elongated body.

9. The needle shield device of claim 1, wherein needle housing includes adhesive tape that seals a distal portion of the straight slot.

10. The needle shield device of claim 1, wherein the needle hub forms a flashback chamber.

11. The needle shield device of claim 1, wherein the elongated body and the inner sleeve are cylindrical.

12. A catheter system comprising:
a catheter assembly comprising a catheter adapter and a catheter extending distally from the catheter adapter; and
a needle shield device that is selectively coupled to the catheter assembly, the needle shield device comprising:
a needle assembly that includes a needle hub, a needle grip disposed around the needle hub and an introducer needle extending distally from the needle hub; and
a needle housing to which the needle assembly is slidably coupled such that, when the needle assembly is slid from a distal position to a proximal position relative to the needle housing, a distal tip of the introducer needle is retracted into the needle housing;
wherein the needle housing comprises:
an elongated body having a straight slot that extends from a proximal end of the elongated body to a distal end of the elongated body; and
an inner sleeve that is positioned within the elongated body and configured to rotate within the elongated body, the inner sleeve including a curved slot that extends from a proximal end of the inner sleeve to a distal end of the inner sleeve;
wherein the needle grip includes a protuberance that extends inwardly through the straight slot of the elongated body and the curved slot of the inner sleeve such that, as the needle assembly is slid from the distal position to the proximal position, the protuberance slides within the straight slot and the curved slot to thereby cause the inner sleeve to rotate relative to the elongated body, the rotation of the inner sleeve relative to the elongated body causing the inner sleeve to cover the straight slot at a distal end of the elongated body.

13. The catheter system of claim 12, wherein the elongated body includes an internal step towards the proximal end of the elongated body and the inner sleeve includes a flange at the distal end of the inner sleeve, and wherein the flange contacts the internal step when the inner sleeve is positioned within the elongated body.

14. The catheter system of claim 12, wherein the protuberance is positioned at a distal end of the straight slot and a distal end of the curved slot when the needle housing is in the distal position.

15. The catheter system of claim 12, wherein the needle housing includes a nose portion that is coupled to the distal end of the elongated body.

16. The catheter system of claim 15, wherein the nose portion is configured to couple to a catheter adapter.

17. The catheter system of claim 15, wherein the nose portion includes one or more grooves that are configured to direct blood away from the straight slot.

18. The catheter system of claim 12, wherein the nose portion includes an elongated extension that seals a distal portion of the straight slot.

19. The catheter system of claim 12, wherein the needle housing includes a septum disposed within the elongated body.

20. The catheter system of claim 12, wherein needle housing includes adhesive tape that seals a distal portion of the straight slot.

\* \* \* \* \*